United States Patent
Uchida

(10) Patent No.: US 9,124,070 B2
(45) Date of Patent: Sep. 1, 2015

(54) SUPERLUMINESCENT DIODE AND OPTICAL COHERENCE TOMOGRAPHY APPARATUS INCLUDING THE SUPERLUMINESCENT DIODE

(71) Applicant: CANON KABUSHIKI KAISHA, Tokyo (JP)

(72) Inventor: Takeshi Uchida, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 23 days.

(21) Appl. No.: 13/720,777

(22) Filed: Dec. 19, 2012

(65) Prior Publication Data
US 2013/0208749 A1    Aug. 15, 2013

(30) Foreign Application Priority Data
Feb. 13, 2012   (JP) .................. 2012-028730

(51) Int. Cl.
| | | |
|---|---|---|
| H01S 5/00 | (2006.01) | |
| H01S 5/34 | (2006.01) | |
| H01S 5/028 | (2006.01) | |
| H01L 33/10 | (2010.01) | |
| H01L 33/00 | (2010.01) | |
| H01L 33/20 | (2010.01) | |
| G01N 21/47 | (2006.01) | |

(52) U.S. Cl.
CPC .............. *H01S 5/34* (2013.01); *H01L 33/0045* (2013.01); *H01L 33/10* (2013.01); *H01S 5/028* (2013.01); *H01S 5/0282* (2013.01); *H01S 5/0285* (2013.01); *G01N 21/4795* (2013.01); *H01L 33/20* (2013.01)

(58) Field of Classification Search
CPC ...... H01S 5/0285; H01S 5/0282; H01S 5/028
USPC .................. 372/49.01, 45.01, 43.01
See application file for complete search history.

(56) References Cited

U.S. PATENT DOCUMENTS

| | | | |
|---|---|---|---|
| 8,472,496 B2 * | 6/2013 | Ledentsov | 372/50.124 |
| 2003/0006429 A1 * | 1/2003 | Takahashi et al. | 257/200 |
| 2003/0210722 A1 * | 11/2003 | Arakida et al. | 372/49 |
| 2004/0213314 A1 * | 10/2004 | Kunitsugu et al. | 372/49 |

(Continued)

FOREIGN PATENT DOCUMENTS

| | | |
|---|---|---|
| JP | 62-2676 A | 1/1987 |
| JP | 2009-283736 A | 12/2009 |

OTHER PUBLICATIONS

Electronics Letters, vol. 32, No. 3, p. 255, 1996.

(Continued)

*Primary Examiner* — Kinam Park
(74) *Attorney, Agent, or Firm* — Fitzpatrick, Cella, Harper & Scinto

(57) ABSTRACT

A superluminescent diode which amplifies light through stimulated amplification and outputs emitted beams from one of edges at two ends includes a cladding layer of a first conductivity type formed on a semiconductor substrate, an active layer formed on the cladding layer of the first conductivity type, a cladding layer of a second conductivity type formed on the active layer, and a multilayer film formed at the other edge opposite to the one edge that emits the beams, reflectance of which has wavelength dependence, and a spectral shape of the emitted beams output from the one edge is controllable by the multilayer film.

18 Claims, 8 Drawing Sheets

(56) References Cited

U.S. PATENT DOCUMENTS

2007/0189348 A1* 8/2007 Kovsh et al. ............... 372/45.01
2011/0075694 A1* 3/2011 Yoshizumi et al. ........ 372/45.01
2013/0056621 A1 3/2013 Suga et al.

OTHER PUBLICATIONS

Semenov, A.T., et al., Spectral Control in Multisection AlGaAs SQW Superluminescent Diodes at 800nm, Electronics Letters, vol. 32, No. 3, pp. 255-256, 1996.

* cited by examiner

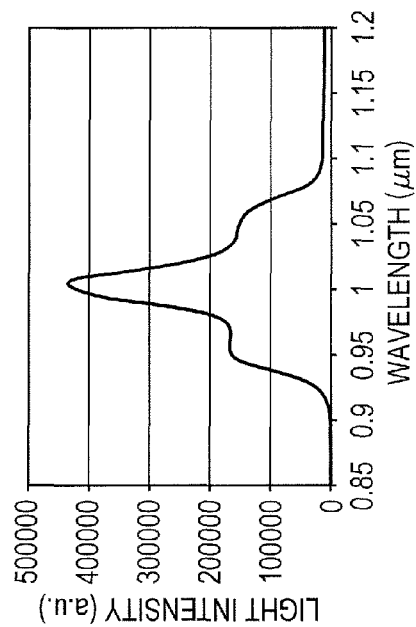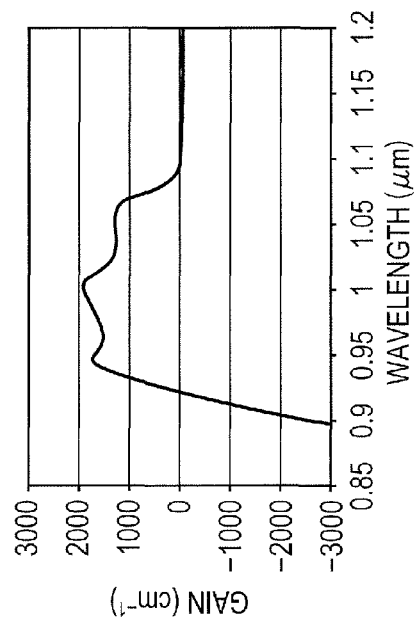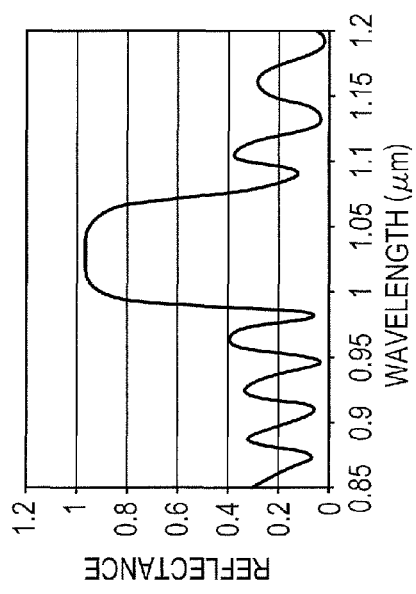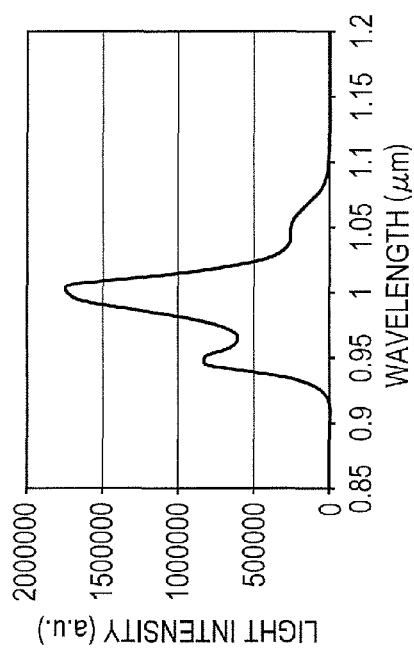

SUPERLUMINESCENT DIODE AND OPTICAL COHERENCE TOMOGRAPHY APPARATUS INCLUDING THE SUPERLUMINESCENT DIODE

BACKGROUND OF THE INVENTION

1. Field of the Invention

The present invention relates to a superluminescent diode and an optical coherence tomography apparatus including the superluminescent diode.

2. Description of the Related Art

As a method for obtaining a tomographic image of an object or a living body, a method called OCT (Optical Coherent Tomography) is known. Since an OCT system (apparatus) is nondestructive and noninvasive, it can be used in, e.g., inspection of industrial products and diagnosis in the field of medicine. Among such OCT systems, a system called SD-OCT (spectral domain OCT) generally uses a spectrometer-based method as disclosed in Japanese Patent Application Laid-Open No. 2009-283736 in which light is emitted from a light source with a broad spectral bandwidth, and the spectrum of beams which interfere with each other is obtained by an OCT optical system. As described in Japanese Patent Application Laid-Open No. 2009-283736, the resolution in a tomographic image increases with an increase in a spectral width to be obtained in an SD-OCT. Accordingly, broadband light sources are required in SD-OCT system applications.

In an OCT optical system, light from a light source needs to be coupled to an optical fiber. The properties required for a light source are thus that the light source has a broad spectral bandwidth and that the light source can be efficiently optically coupled to an optical fiber. Examples of such a light source that is coupled to an optical fiber and that has a broad spectral bandwidth include a semiconductor device called a superluminescent diode (hereinafter also referred to as an SLD).

An SLD is configured to emit light from an edge, like a normal semiconductor laser. The principle of operation of the SLD is that current injection causes a population inversion in an active layer to emit light through stimulated amplification resulting from the population inversion, as in the operation of a semiconductor laser. Note that the SLD is different from a semiconductor laser in that, for the sake of preventing resonance phenomena, the SLD is configured without a pair of reflecting mirrors for resonance. For this reason, in the SLD, light is amplified by stimulated amplification during back and forth propagation or one-way propagation of the light between ends of a waveguide structure which is formed in a semiconductor, and then the light is emitted from an edge.

A plurality of types of structures is available as the structure of an active layer of an SLD. One of the structures is an active layer structure often used in a normal semiconductor laser, as in ELECTRONICS LETTERS, Vol. 32, No. 3, p. 255, 1996. More specifically, the active layer structure includes a plurality of quantum wells, having the same structure, arranged in an active layer. Another one is called an asymmetric multiple quantum well or a modulated multiple quantum well, in which a plurality of quantum well layers different in emission wavelength (ground-state emission wavelength to be exact) is incorporated as an active layer in one waveguide structure. Japanese Patent Application Laid-Open No. 2009-283736 discloses an SLD using two quantum wells different in emission wavelength as an active layer for bandwidth broadening, and the SLD has achieved a wavelength width of 84 nm.

Depending on required properties of an applied system, a specific spectral shape may be required as well as wavelength band. For example, in an SD-OCT system, the spectral shape of a light source as well as bandwidth broadening affects the quality of a final tomographic image.

Since an obtained spectrum is to be converted into a tomographic image by a Fourier transform, a desired spectral shape of a light source may be a unimodal spectral shape (desirably the spectral shape may be analogical to the shape of a Gaussian function). Such a spectral shape inhibits deterioration of an S/N ratio at the time of a Fourier transform or formation of an artifact which does not occur naturally, and thus it allows improvement in the quality of a tomographic image.

As described above, there is an optimum spectral shape for a light source in an OCT system. An SLD serving as a light source is expected to satisfy the requirement.

SUMMARY OF THE INVENTION

As described in Japanese Patent Application Laid-Open No. 2009-283736, a wavelength band of several tens of nm sufficient to satisfy OCT applications has been achieved in an SLD which is an actually used light source. However, the spectral shape of the SLD cannot be arbitrarily controlled according to the requirement of the system.

The process of determining a spectral shape has some relations with the problem of the inability to arbitrarily control a spectral shape. In a structure in which a single quantum well or a plurality of quantum wells having the same structure is introduced, as in ELECTRONICS LETTERS, Vol. 32, No. 3, p. 255, 1996, since an SLD generates light through stimulated amplification, an emission spectrum from the quantum well(s) depends on the wavelength dependence of stimulated amplification that occurs in the quantum well(s) (hereinafter referred to as a gain spectrum). The gain spectrum is determined by multiplication of the energy distribution of carriers in the quantum well(s), i.e., so-called a Fermi-Dirac distribution and the density of states of the quantum well(s), specifically the rectangular shape of the density of states. Since the two factors are determined by quantum mechanics and material property, free artificial control of the shape is impossible. For this reason, as illustrated by a calculation example in Example 1 (to be described later) implemented by the present inventor, although the bandwidth of a spectrum can be broadened by an increase in injection level, the shape of the spectrum cannot be freely adjusted to, e.g., a unimodal shape that is desirable for OCT applications.

If an active layer is formed to have an asymmetric multiple quantum well structure with different ground-state emission wavelengths, as in Japanese Patent Application Laid-Open No. 2009-283736, a spectral shape can be controlled to a certain degree. For example, the emission intensity of long wavelength light can be increased by providing much number of quantum wells which emit beams at long wavelengths compared to the short wavelength quantum wells.

However, as described above, the gain spectrum of each quantum well has a fixed shape, which cannot be artificially and freely controlled. For this reason, even if an asymmetric multiple quantum well structure is introduced to control a gain spectrum, a range within which the gain spectrum can be controlled is just a range that is obtained by combining the gain spectra of quantum wells. It is difficult to freely adjust the shape to a requirement of an application (e.g., a unimodal spectral shape for an OCT application).

Additionally, if drive current is increased to gain increased optical output power, a larger number of carriers will be present in higher states, and when the drive current reaches a certain level, the intensity of light emission on the short wavelength side, due to light emission from a first state, becomes higher. Thus, it will be difficult to achieve a unimodal spectral shape having a peak at the center. For this reason, if injection at this level is required for an optical output, a gain spectrum is automatically determined, and control of the gain spectrum only is impossible. This is also due to the gain spectrum of a quantum well (quantum wells) being subject to quantum mechanics and material property. The little number of parameters for controlling the shape of a gain spectrum leads to the difficulty in solving the problems.

In consideration of the above-described problems, the present invention has as an object to provide a superluminescent diode whose spectral shape can be freely controlled, regardless of quantum mechanics and material property, and an OCT apparatus including the superluminescent diode.

A superluminescent diode according to the present invention is a superluminescent diode which amplifies light through stimulated amplification and outputs emitted beams from one of edges at two ends, including a cladding layer of a first conductivity type formed on a semiconductor substrate, an active layer formed on the cladding layer of the first conductivity type, a cladding layer of a second conductivity type formed on the active layer, and a multilayer film formed at the other edge opposite to the one edge that emits the beams, reflectance of which has wavelength dependence, wherein a spectral shape of the emitted beams output from the one edge is controllable by the multilayer film.

An OCT apparatus according to the present invention includes the above-described superluminescent diode.

According to the present invention, it is possible to implement a superluminescent diode, a spectral shape of which can be freely controlled, regardless of quantum mechanics, material property, and the like, and an OCT apparatus including the superluminescent diode.

Further features of the present invention will become apparent from the following description of exemplary embodiments with reference to the attached drawings.

BRIEF DESCRIPTION OF THE DRAWINGS

FIGS. 7A, 7B, 7C, and 7D are graphs for describing reflectance, spectral shapes, and a gain spectrum from an SLD according to Example 3 of the present invention.

DESCRIPTION OF THE EMBODIMENTS

Figure 1A:
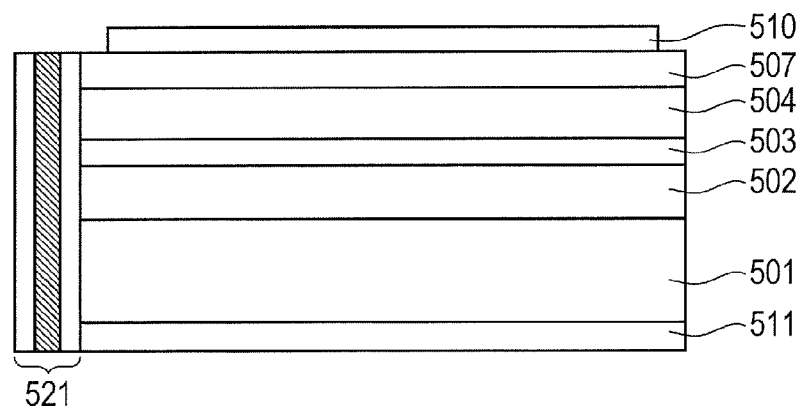
FIGS. 1A, 1B, and 1C are views and a graph for describing a semiconductor layer structure of an SLD according to Example 1 of the present invention.

Preferred embodiments of the present invention will now be described in detail in accordance with the accompanying drawings.

In an SLD, in general applications, light to be utilized is emitted from one of edges at two ends and taken into an optical fiber. For example, in the case of an SD-OCT system (or apparatus), light to be utilized is emitted from one edge, taken into an optical fiber, and introduced to an interference system and an object to be measured. In the following description, an edge from which light taken into a system or the like and utilized is emitted will be referred to as a front edge, and the other edge on the opposite side will be referred to as a rear edge.

In a superluminescent diode (SLD), light is amplified by stimulated amplification at an active layer, and the amplified light accounts for a large part of light to be emitted. The stimulated amplification increases exponentially with an increase in distance. For this reason, if the device length of an SLD is changed while the amplification factor of stimulated amplification remains unchanged, optical output power increases sharply with an increase in device length.

Consider here a case where the reflectance changes at a rear edge of an SLD. If the reflectance at a front edge is 0, and the reflectance at a rear edge is also 0, a distance over which light is subjected to stimulated amplification in the SLD before the light is emitted is at most identical to the device length (a length in a light propagation direction). If the reflectance at the front edge is 0, and the reflectance at the rear edge is 1.0, the distance over which light is subjected to stimulated amplification in the SLD before the light is emitted is at most twice the device length. This at most length is achieved when light emitted by spontaneous emission around the front edge propagates toward the rear edge while the light is amplified by stimulated amplification, reflected by the rear edge, propagates toward the front edge while the light being amplified by stimulated amplification, and then emitted from the front edge. If the rear edge has a reflectance intermediate between 0 and 1.0, a phenomenon intermediate between the two cases occurs.

As described above, since light is amplified exponentially with an increase in propagation distance in an SLD, the optical output power at a front edge increases more than two-fold when the reflectance at a rear edge is varied from 0 to 1.0.

The present inventor noted that the optical output power at a front edge could be greatly increased or reduced by controlling the reflectance at a rear edge.

According to the present inventor's thought experiment on a case where the reflectance at a rear edge varies according to wavelength, it was found from the above-described mechanism that amplification factors for respective wavelengths could be effectively controlled for a device as a whole by causing the reflectance at the rear edge to have wavelength dependence. That is, as above, the amplification factor of the SLD as a whole is determined by multiplication of an amplification factor at the time of light propagation from a front edge to the rear edge which is determined by a gain spectrum, the reflectance at the rear edge, and an amplification factor at the time of propagation from the rear edge to the front edge. Therefore, through control of a wavelength distribution at the rear edge to control the shape of the reflectance spectrum at the rear edge, the wavelength dependence of the light amplification factor of the SLD as a whole could be controlled. From this, the present inventor found the new artificially controllable method, i.e., the amplifying characteristic of an SLD, which is determined by the physical properties of a quantum well and material parameters, can be controlled using the reflectance at a rear edge that is a factor external to a semiconductor material.

As described earlier, a unimodal spectrum is desirable in OCT applications. the present invention enables to bring out the spectral shape of the SLD close to the desirable spectral shape, by comparing the shape of the spectrum of an SLD, which is determined by the intrinsic gain distribution of an active layer, with a spectral shape desirable for a system such as an OCT system, and correcting the difference between the spectral shapes with a reflectance distribution at a rear edge.

The present invention has also the advantage of small energy loss at the time of spectral shape control, as well as the above advantage of the ability to control a spectral shape. For the sake of explanation thereof, energy lost at the time of controlling spectral shape in a configuration in which the reflectance at a rear edge is varied, and energy lost at the time of controlling spectral shape in a configuration in which light emitted from a front edge is passed through an optical filter with wavelength dependant transmittance for wavelength selection, will be compared.

Figure 2A:
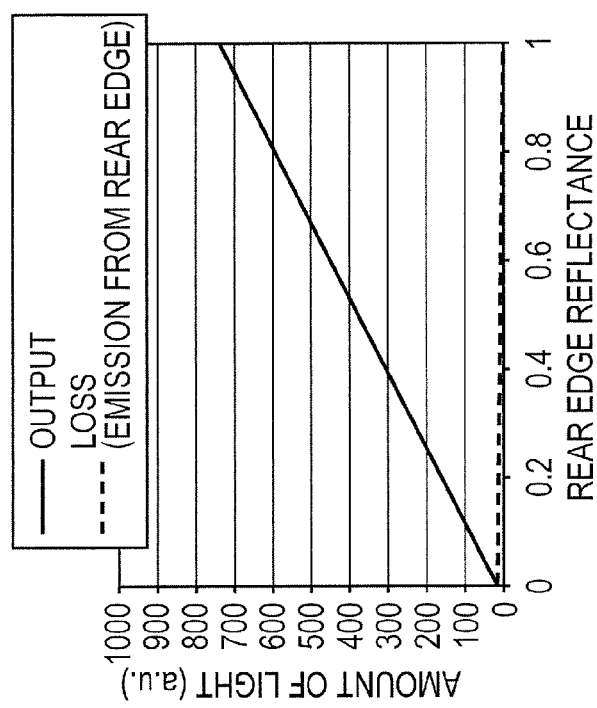
FIGS. 2A and 2B are graphs for describing comparison between emitted beams and energy losses in two forms of embodiment of the present invention.

A calculation example of changes in optical output power at a front edge and a rear edge in an embodiment of the present invention when the reflectance at the rear edge is varied is illustrated in FIG. 2A. The relationship between the optical absorbance at an optical filter with wavelength dependant transmittance (e.g., a filter in Japanese Patent Application Laid-Open No. 562-2676 as the prior art) and the amount of light output to a fiber in a configuration in which light emitted from a front edge is passed through the filter for wavelength selection is illustrated in FIG. 2B.

Figure 2B:
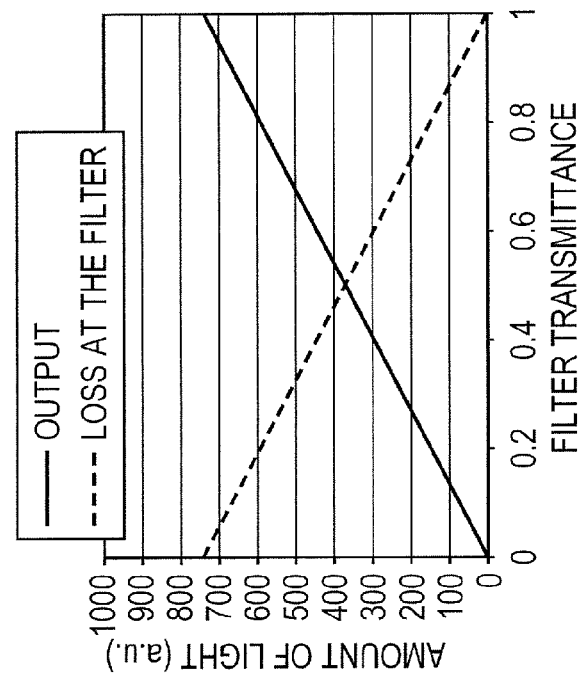

FIGS. 2A and 2B illustrate the amount of light loss by emission from the rear edge (the configuration according to the present invention) and the amount of light loss by absorption at the optical filter with wavelength dependant transmittance (the configuration in Japanese Patent Application Laid-Open No. S62-2676), together with optical output power output from the front edges. As illustrated in FIG. 2A, it can be seen that, in the configuration according to the present invention in which the reflectance at the rear edge is varied, through the variation of the reflectance from 0 to 1.0, a change in the amount of light emitted from the front edge is larger than a loss from the rear edge. In contrast, in the case of FIG. 2B, since all the beams which do not pass through the filter will be the loss, an amount of reduced optical output power will all be the loss.

The proportion of the energy of emitted light to total energy input to a device at the time of spectral shape control will be considered.

In the case of the configuration according to the present embodiment, since the reflectance at the rear edge is made to vary according to wavelength, even when the amount of light at a certain wavelength is reduced, as illustrated in FIG. 2A, the amount of light existing as a loss from the rear edge is small. That is, for the device as a whole, a light amplification factor is low at the wavelength while an amplification factor at a wavelength with a high reflectance can be regarded as high. Since this phenomenon occurs in a single active layer, a more amount of input energy is converted into beams at wavelengths with high amplification factors, and thus a spectral shape can be efficiently changed.

If a spectral shape is controlled by passing light emitted from a device through an optical filter with wavelength dependant transmittance, as described in Japanese Patent Application Laid-Open No. S62-2676, beams absorbed by the filter for spectrum control are all lost, as illustrated in FIG. 2B. For this reason, the proportion of beams to be lost to all the beams input to the device is large, and the amount of light emitted to a fiber is small.

As can be seen, the electricity-to-light conversion efficiency under spectral shape control in a case where spectral shape control is performed with the configuration according to the present invention is advantageously higher than the electricity-to-light conversion efficiency in a configuration as in Japanese Patent Application Laid-Open No. S62-2676.

EXAMPLES

Examples of the present invention will be described.

Example 1

A configuration example of an SLD according to the present invention will be described as Example 1 with reference to FIGS. 1A to 1C.

As illustrated in FIG. 1A, the vertical layer configuration of an SLD according to the present example is such that layers are stacked on a semiconductor substrate in the manner below. More specifically, an n-cladding layer 502 (a cladding layer of a first conductivity type) made of $Al_{0.5}Ga_{0.5}As$ is arranged on a GaAs substrate 501. An active layer 503 including one InGaAs/GaAs quantum well (not shown) is located on the n-cladding layer 502. The active layer 503 includes one quantum well layer and its emission wavelength in a ground state is 1050 nm. A p-cladding layer 504 (a cladding layer of a second conductivity type) made of p-type $Al_{0.5}GaAs$ is arranged on the active layer 503. A contact layer 507 having a thickness of 10 nm and made of heavily doped p-type GaAs is located on the p-cladding layer 504. An upper electrode 510 kept in electrical contact with the contact layer 507 lies on the contact layer 507. A lower electrode 511 kept in electrical contact with the substrate 501 lies on a lower surface of the substrate.

Figure 1B:
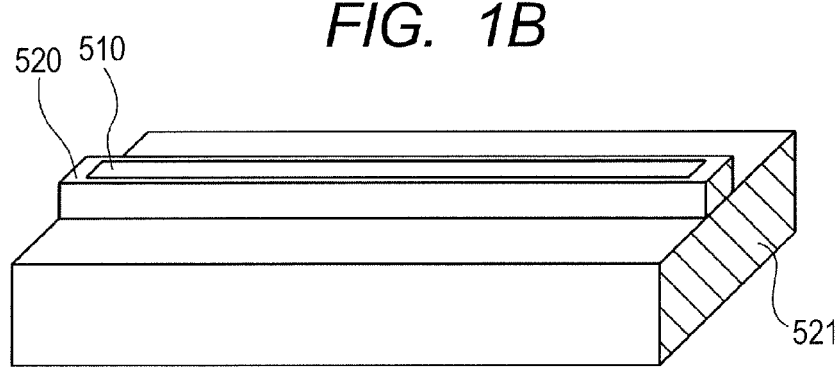
Figure 1C:
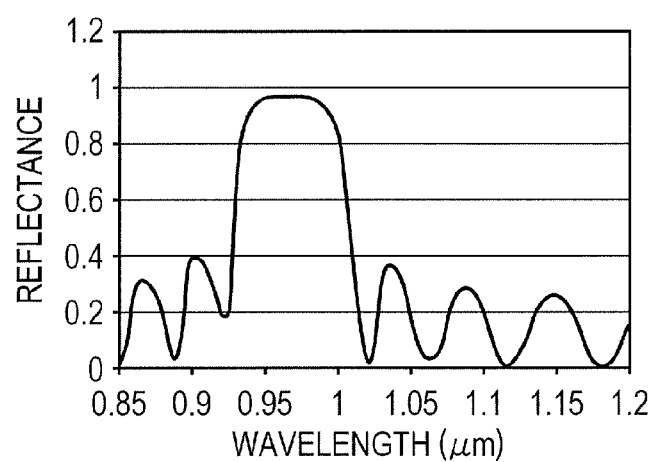

As illustrated in FIG. 1B, the device shape of the SLD according to the present example is such that the p-cladding layer 504 and contact layer 507 are partially removed to the middle of the p-cladding layer while left parts form a ridge 520 having a width of 4 μm. The device length is 0.3 mm, and the upper electrode 510 is formed on the ridge. Edges of the ridge are cleaved facets of the GaAs crystals, and the two GaAs cleaved facets are perpendicular to an optical waveguiding direction, which is determined by the structure of the ridge. A so-called AR coating for lowering reflectance is applied to a front edge while a multilayer film 521 for controlling a reflectance spectrum is attached to a rear edge. The multilayer film 521 is formed as a distributed Bragg reflector (DBR) having a center wavelength of 965 nm by stacking 20 pairs of two types of $SiO_xN_y$ having refractive indices of 1.5 and 1.6. A reflectance spectrum achieved by the multilayer film 521 is illustrated in FIG. 1C.

Figure 3:
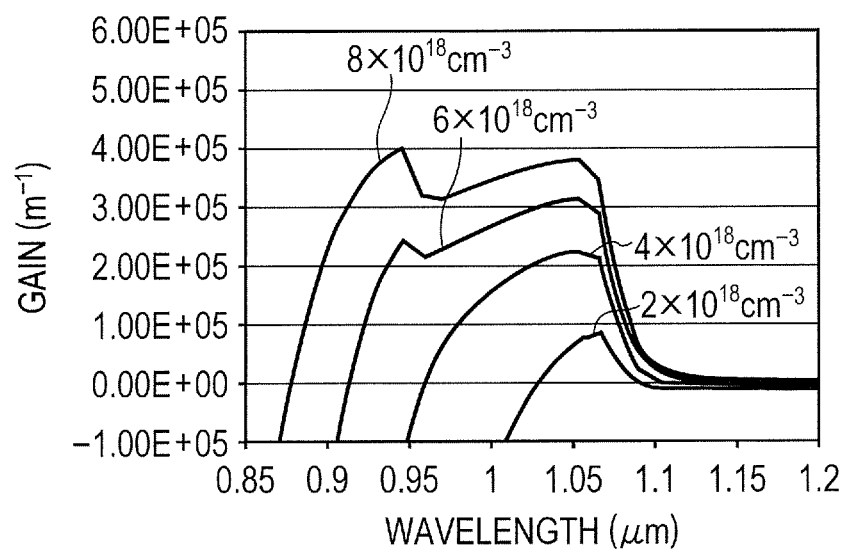
FIG. 3 is a graph for describing the carrier density dependence of a gain spectrum of a quantum well according to Example 1 of the present invention.

FIG. 3 illustrates the gain spectrum of the active layer according to the present example, as well as the carrier density dependence of the gain spectrum. When the carrier density is low, light emission around 1050 nm corresponding to the ground state, which is from the long wavelength side, is observed. Light emission from a first state corresponding to around 930 nm increases with an increase in carrier density. When the carrier density is about 6 to $8\times10^{18}$ $cm^{-3}$, a comparable intensities of light emission from are observed in the two states. In the present example, the multilayer film 521 at the rear edge is designed and loaded such that a spectrum output by the SLD approaches unimodality, which is desirable for a system, when the SLD is driven with a carrier density of $6 \times 10^{18}$ cm$^{-3}$, that is a drive condition for the SLD.

Specific design principles will be described later.

Figure 4A:
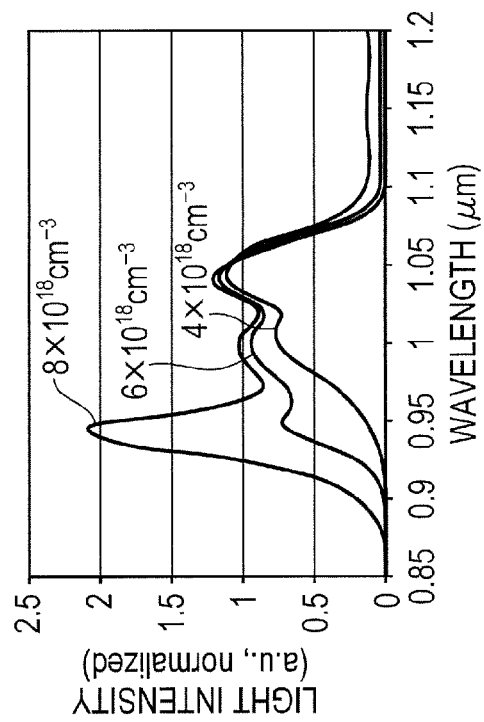
FIGS. 4A and 4B are graphs for describing the spectra of emitted beams from the SLD according to Example 1 of the present invention.
Figure 4B:
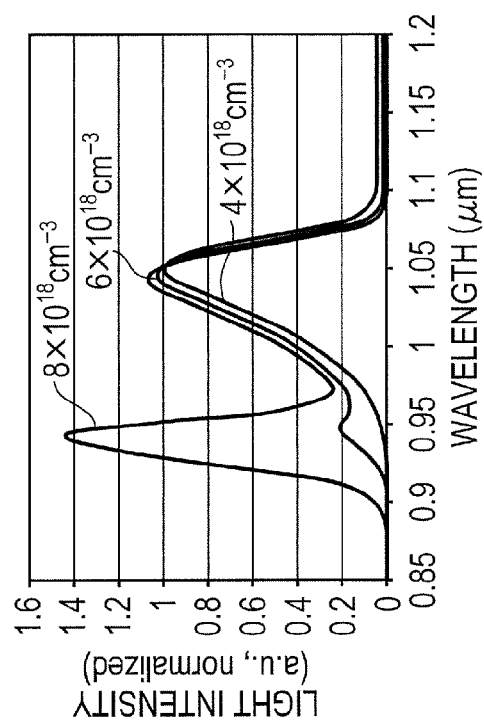

Results of calculating the spectral shapes of light emitted from the front edge of the SLD with the above-described device structure for, a case where the rear edge constitutes a reflecting mirror whose reflectance does not have wavelength dependence, and a case where the rear edge has a reflectance spectrum achieved by the multilayer film 521 according to the present example, are illustrated in FIGS. 4A and 4B.

As for FIG. 4A, the reflectance at the rear edge is 0.3, regardless of wavelength. As for FIG. 4B, the multilayer film 521 described earlier is loaded.

In FIG. 4A, when the carrier density is relatively low, light is emitted only from the ground state. When the carrier density increases, light emission from the first state is observed. It can be seen that, although the increase in carrier density broadens the width of an emission wavelength band, there is a large dip at the center, and the dip cannot be filled in by increasing or reducing the carrier density. Since such a dip is determined by the above-described multiplication of a distribution of carriers and the density of states of a quantum well, the dip is not a phenomenon intrinsic in the quantum well according to the present example, rather it is a phenomenon common among quantum well structures. Therefore, even if the configuration is changed in, e.g., the width of the quantum well or the material, the dip cannot be eliminated.

When the carrier density is low, the case where the multilayer film 521 is loaded, as illustrated in FIG. 4B, is not much different from the case in FIG. 4A. However, it can be seen that when the SLD is driven with a carrier density of $6 \times 10^{18}$ cm$^{-3}$ at which light emission from the first state corresponding to around 930 nm increases, the spectral shape of the SLD approaches unimodality and thus it is closer to a spectral shape required by an OCT application. When the SLD is driven with a carrier density of $8 \times 10^{18}$ cm$^{-3}$, the intensity of light emission on the short wavelength side is high, and the spectral shape is not unimodal. However, there is no dip at the center, which shows the influence of spectral shape control by the multilayer film 521.

Two design principles are set for the multilayer film 521 used in emission spectral shape control of the SLD.

One of the principles is that a high reflectance band with high reflectance at the rear edge be set so as to cover a wavelength which has a gain lower than gains of surroundings, between the wavelengths corresponding to the ground state and first state, specifically to cover a wavelength corresponding to a dip, i.e., a local minimum, in the gain spectral shape intrinsic in the quantum well. It can be seen from FIG. 3 that a local minimum is present around 960 nm in the present example. In FIG. 4A, the spectrum of the SLD also has a dip corresponding to the local minimum. The high reflectance band herein refers to a wavelength band between: the maximum value of the reflectance; and two wavelengths (present on the short wavelength side and the long wavelength side, respectively, of a wavelength with the maximum reflectance) with reflectances intermediate between the maximum value and local minimums (which are closest to the maximum reflectance) of the reflectance. For example, in FIG. 1C, the high reflectance band covers 930 nm to 1010 nm.

The other of the principles is that the variability in the reflectance at the rear edge exceeds 10% within a range where the gain spectrum is positive, i.e., a range where amplification, not absorption, occurs. If the reflectance does not vary, amplification occurs at all wavelengths, and the spectral shape at the front edge cannot be controlled.

In order to reduce laser oscillation, the reflectance of the AR coating at the front edge is desirably not more than 0.05. A smaller value is required to reduce ripples in the SLD spectrum.

The position of a dip in an SLD emission spectrum varies according to the drive condition and thus it is not uniquely determined. However, in an SLD including a single quantum well or a plurality of quantum wells having the same structure as in the present example, a population inversion often occurs between the ground state and the first state due to limitations such as thermal saturation, which produces a dip between the wavelengths for the states. It is thus useful to bring the maximum value of the reflectance at the rear edge within a wavelength band between the wavelengths for the two states. With this configuration, a spectrum to be output by an SLD can be flattened and be made unimodal. In the present example, the maximum value of the reflectance at the rear edge is located between the wavelengths for the ground state and first state.

A device fabrication procedure according to the present example will be described below.

First, the n-cladding layer 502, active layer 503, p-cladding layer 504, and contact layer 507 are grown as a semiconductor layer configuration on the GaAs substrate 501 by metalorganic vapor phase epitaxy or molecular beam epitaxy. A dielectric film is formed on the wafer by sputtering. After that, a stripe formation mask for ridge formation is formed with a photoresist by semiconductor photolithography. A semiconductor part other than the stripe formation mask is selectively removed by dry etching to form a ridge having a height of 0.5 μm. After that, SiO$_2$ is formed on the semiconductor surface, and SiO$_2$ on the ridge is partially removed by photolithography. The p-side and n-side electrodes 510 and 511 are formed by vacuum evaporation method and photolithography. The electrodes and semiconductor are alloyed under a high temperature nitrogen atmosphere in order to achieve good electrical characteristics.

Finally, the device is cleaved to have a crystal facet at each edge, and the two edges are coated with dielectric films for reflectance adjustment. A general AR coating is applied to the front edge, and the multilayer film 521 for controlling a reflectance spectrum that is formed as a DBR having a center wavelength of 965 nm by stacking 20 pairs of two types of SiO$_x$N$_y$ having refractive indices of 1.5 and 1.6 is formed at the rear edge.

The dielectric films are applied to the front and rear cleave surfaces, and thus a device is completed.

Figure 8:
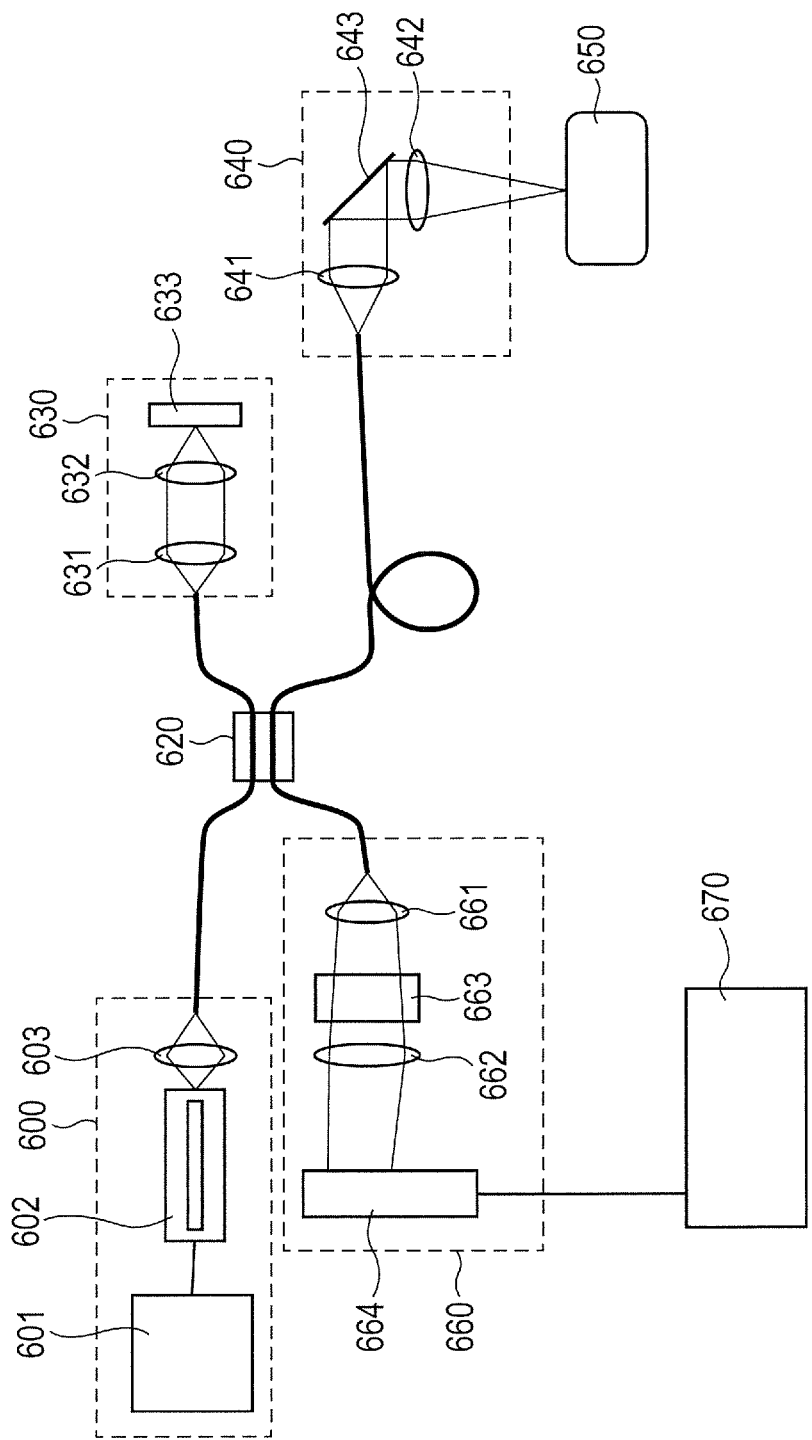
FIG. 8 is a diagram for describing an SD-OCT system using the SLD according to Example 1 of the present invention.

An SD-OCT system (optical coherence tomography apparatus) including an SLD which is a superluminescent diode thus fabricated as a light source is illustrated in FIG. 8. The system includes a light source section 600, an optical coupling section 620 which optically couples fibers, a reference light optical system 630, an irradiation optical system 640 for irradiating an object 650 to be measured with light, a spectrometer 660, and an image conversion section 670 which converts spectral information into an image.

The light source section 600 includes a drive circuit 601, an SLD 602 illustrated in FIGS. 1A and 1B, and a lens 603 which couples light to an optical fiber. Light emitted from the SLD 602 enters the optical fiber through the lens 603. A component of the light obtained through split-up by the optical coupling section 620 enters the reference light optical system 630. The reference light optical system 630 includes collimator lenses 631 and 632 and a reflecting mirror 633. The component is reflected by the reflecting mirror 633 and enters the optical fiber. The other component of the light from the optical fiber obtained through split-up by the optical coupling section 620 enters the irradiation optical system 640. The irradiation optical system 640 includes collimator lenses 641 and 642 and a reflecting mirror 643 for bending an optical path by 90°. The irradiation optical system 640 is responsible for bringing incoming light onto the object 650 to be measured and coupling again reflected light to an optical fiber.

The components from the reference light optical system 630 and irradiation optical system 640 pass through the optical coupling section 620 and enter the spectrometer 660. The spectrometer 660 includes collimator lenses 661 and 662, a grating 663 for spectral diffraction, and a line sensor 664 for obtaining spectral information of light diffracted by the grating 663. The spectrometer 660 is configured to obtain spectral information of incoming light. The information obtained by the spectrometer 660 is converted into an image by the image conversion section 670 for reconstructing a tomographic image of the object 650 to be measured, and tomographic image information as a final output is obtained.

Example 2

Figure 5:
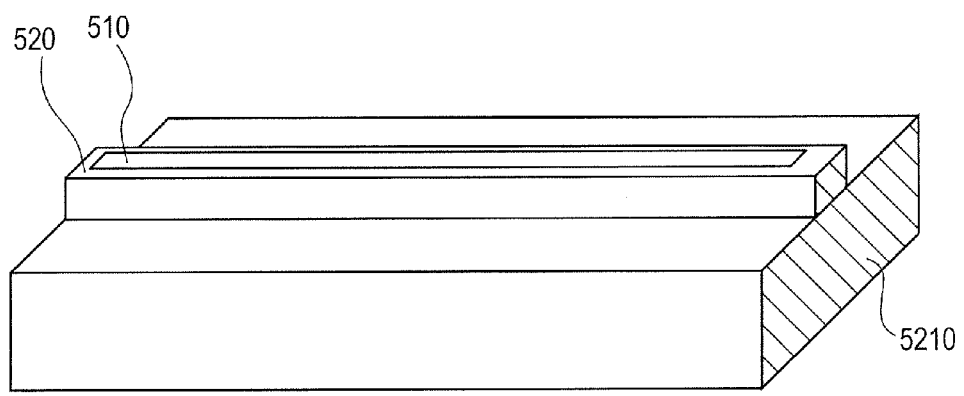
FIG. 5 is a view for describing an SLD device structure according to Example 2 of the present invention.

A configuration example of an SLD in a form different from Example 1 will be described as Example 2 with reference to FIG. 5. In the present example, the semiconductor layer configuration is the same as in Example 1 except that an asymmetric multiple quantum well is used for a quantum well layer. For this reason, only a difference from Example 1 and a difference in influence on an SLD emission spectrum brought about by the difference will be described. Note that the same members are denoted by the same reference numerals.

In the present example, two quantum wells (not shown) different in ground-state emission wavelength are used. The emission wavelengths of the quantum wells are 1050 nm and 930 nm, respectively. The SLD is configured such that carriers are accumulated with a carrier density of $3 \times 10^{18}$ cm$^{-3}$ in the quantum well having the emission wavelength of 930 nm, at an injected current value where carriers are accumulated with a carrier density of $5 \times 10^{18}$ cm$^{-3}$ in the quantum well having the emission wavelength of 1050 nm. In the present example, this state is a drive condition for the device.

A multilayer film 5210 at a rear edge has a center wavelength of 990 nm. The refractive indices of layers and the number of stacked pairs are the same as in Example 1. The device length is 0.5 mm, unlike Example 1. Control that makes the carrier density of the quantum well on the short wavelength side lower than the carrier density of the quantum well on the long wavelength side in the asymmetric multiple quantum well is implemented by utilizing a phenomenon that, when quantum well width is reduced, a ground state is raised and the rate of transition from a barrier layer to a well layer is lowered.

Figure 6A:
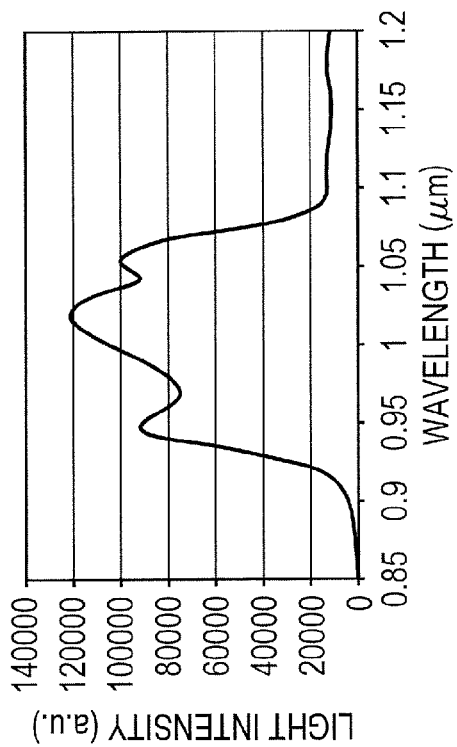
FIGS. 6A and 6B are graphs for describing spectral shapes of emitted beams from the SLD according to Example 2 of the present invention.
Figure 6B:
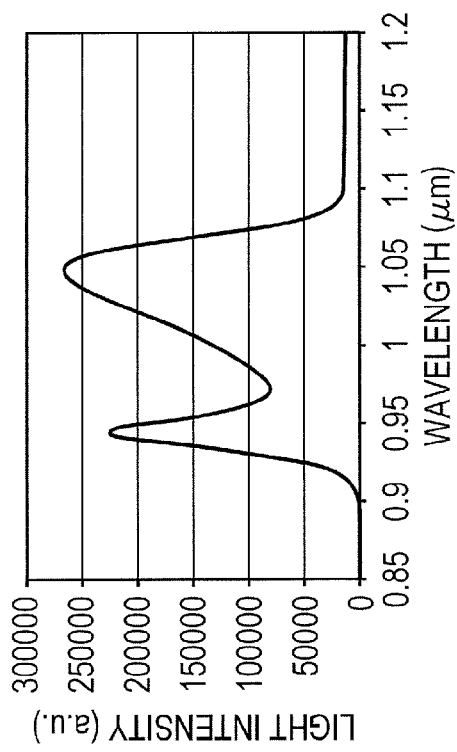

Results of calculating the spectral shape of light emitted from a front edge of the SLD under the drive condition for the device, for a case where the rear edge constitutes a reflecting mirror whose reflectance does not have wavelength dependence and, for a case where the rear edge has a reflectance spectrum achieved by the multilayer film 5210 according to the present example, are illustrated in FIGS. 6A and 6B. FIG. 6A illustrates a case where the reflectance at the rear edge is 0.3, regardless of wavelength while FIG. 6B illustrates a case where the multilayer film 5210 having a center wavelength of 990 nm is used. A comparison between FIGS. 6A and 6B shows that the spectral shape is more unimodal in FIG. 6B.

As described above, when an asymmetric multiple quantum well is incorporated into an SLD, the spectral shape of light emitted by the SLD can be controlled by controlling the reflectance spectrum at a rear edge, and the spectral shape can be close to spectral shapes required by applications. In the present example, the intensity of light emission around 990 nm, that is intermediate between the 0th state wavelengths of the two quantum wells, is enhanced by increasing the reflectance at the rear edge to bring the spectral shape close to a spectral shape required by an application, which in the present example is a unimodal spectral shape required for an OCT application.

Although the intensity of light emission around a wavelength corresponding to a state in each quantum well can be enhanced when an asymmetric multiple quantum well as in the present example is used, the intensity of light emission between the wavelengths for the states cannot be selectively enhanced. This is because each quantum well has a fixed gain spectral shape, as described above, and the spectral shape of the SLD is determined by combining the gain spectra.

Note that since an asymmetric multiple quantum well is used in the present example, a broad wavelength band can be covered by light emission from the 0th states in the quantum wells only. The carrier densities as the drive condition are lower than the carrier density in Example 1, which leads to extension of device life and improvement in reliability.

In the present example, the maximum value of the reflectance is located between the wavelengths corresponding to the two ground states. If quantum wells having three or more different wavelengths in ground states are introduced, the maximum value of the reflectance at a rear edge is desirably set in a wavelength region between the shortest wavelength in the ground state and the longest wavelength in the ground state. This is because, since a population inversion is generated mainly in a wavelength band between the wavelengths, when the maximum value of the reflectance between the wavelengths is set therebetween, wavelength dependence of reflectance can be produced in the wavelength band where population inversion is generated, and thus control of the spectrum of light emitted from an SLD can be effectively performed.

Example 3

A configuration example of an SLD in a form different from the above-described examples will be described as Example 3. In the present example, the semiconductor layer configuration is the same as in Example 1 except that an asymmetric multiple quantum well is used for a quantum well layer. For this reason, only a difference from Example 1 and a difference in influence on an SLD emission spectrum brought about by the difference will be described.

In the present example, three quantum wells different in ground-state emission wavelength are used. The emission wavelengths of the quantum wells are 1050 nm, 990 nm, and 930 nm, respectively. The SLD is configured such that carriers are accumulated with a carrier density of $3 \times 10^{18}$ cm$^{-3}$ in the quantum wells having the emission wavelength of 990 nm and the emission wavelength of 930 nm, at an injected current value where carriers are accumulated with a carrier density of $5 \times 10^{18}$ cm$^{-3}$ in the quantum well having the emission wavelength of 1050 nm. In the present example, this state is a drive condition for the device.

A multilayer film at a rear edge has a center wavelength of 1030 nm, which is a wide difference from Examples 1 and 2.

In Examples 1 and 2, emission intensity has two peak values, and the maximum value of the reflectance at the rear edge is set between wavelengths corresponding to the peak values. In contrast, in the present example, the maximum value of the reflectance at the rear edge is set not around a center in an emission intensity spectrum of the SLD but on the long wavelength side and, more specifically, near a wavelength which is the longest wavelength of the ground states of the quantum wells.

A distribution of reflectance at the rear edge (FIG. 7A), and results of calculating an SLD spectrum under the drive condition for a case where the reflectance at the rear edge is constant (FIG. 7B) and for a case where reflectance control is performed with the loaded multilayer film according to the present example (FIG. 7C), are illustrated. A gain spectrum obtained under the drive condition is illustrated in FIG. 7D. The reflectance at the rear edge is designed as illustrated in FIG. 7A, according to the SLD emission spectrum illustrated in FIG. 7B under the drive condition for the case where the reflectance at the rear edge is not controlled in the present example.

Although the highest carrier density is achieved in the quantum well having the longest wavelength of 1050 nm in the present example, the gain at 1050 nm is lower than a peak among all the quantum wells. As can also be seen from FIG. 3, this is because a quantum well gain is not symmetric about a wavelength corresponding to a peak around a ground state and it is higher on the short wavelength side. As described above, the asymmetry results from a distribution of carrier density and the shape of the density of states.

Due to the asymmetry, if the gain spectra of quantum wells in an asymmetric multiple quantum well structure are combined, the light intensity is higher on the short wavelength side, as illustrated in FIG. 7D.

Although more carriers are injected on the long wavelength side in the present example to solve the problem, the gain spectrum is not completely symmetric. Even if more carriers than in the drive condition of the present example are injected into the quantum well on the long wavelength side, the situation gets worse instead of being overcome. This is because when a quantum well structure has a carrier density above a certain value ($6\times10^{18}$ cm$^{-3}$ in FIG. 3), the intensity of light emission from a first state becomes higher, as illustrated in FIG. 3. A spectral shape cannot be brought closer to unimodality only by adjusting a drive condition.

Under the circumstances, the peak of the reflectance is set to around 1030 nm, which is near the longest wavelength in the ground state of the quantum well in the present example, to control the SLD spectral shape. As a result, it can be seen from FIG. 7C that reflectance control has brought the SLD spectral shape closer to unimodality and also a wavelength band is broadened.

As illustrated in FIG. 7D, local minimums of the gain spectrum are located around 960 nm and 1010 nm under the drive condition for the present example. It can also be seen that the local minimum around 1010 nm is included in a high reflectance band of the rear edge.

As will be appreciated from the description in Examples 1 to 3 described above, reflectance is increased mainly at a wavelength where the gap between an SLD spectral shape obtained from the gain spectrum of a quantum well (quantum wells) under an SLD drive condition and a spectral shape required by an application is large. With this configuration, it is possible to fill the gap and bring the spectrum close to a spectrum required by the application.

As will also be appreciated from the description in Examples 1 to 3, in order to control a spectral shape, the reflectance at a rear edge needs to vary within a range where the gain spectrum of an active layer of an SLD is positive under a drive condition, i.e., a wavelength range where stimulated emission is occurring instead of interband absorption. This is because the range where stimulated emission is occurring is the spectral range of light emitted from the SLD, and the reflectance at the rear edge needs to vary within the range in order to change a spectral shape.

The variability in the reflectance at a rear edge desirably exceeds 10%. As can be seen from FIG. 2A, this is because the optical output power of an SLD varies by about 10% when the reflectance at a rear edge varies from the maximum value by 10%.

A drive condition is determined so as to meet all of restrictions like optical output power and design device life, in addition to a spectral shape. As illustrated in Examples 1 to 3, the optimum shape for a reflectance spectrum may differ according to a condition, depending on device design. However, the above-described idea of, increasing reflectance mainly at a wavelength where the gap between an SLD spectral shape obtained from the gain spectrum of an active layer and a spectral shape required by an application is large to fill the gap, can be similarly applied.

If an active layer has a quantum well structure, the above-described wavelength range where stimulated emission occurs can be rephrased as a range between a longest one of the wavelengths in ground states of quantum wells constituting the active layer and a shortest one of the wavelengths in first states of the quantum wells. As can be seen from FIG. 3, this is because, in up to a first state, it is feasible to accumulate carriers and cause a population inversion with a realistic carrier density in a quantum well structure.

In a second state or a higher state, even if those states appear, generating a population inversion at a wavelength corresponding to the state to cause stimulated amplification is not realistic. For this reason, in the case of an active layer having a quantum well structure, the spectrum of an SLD can be changed as long as a part of a high reflectance band where the reflectance at a rear edge is high is present within the above-described wavelength range, specifically between the shortest wavelength in a first state and the longest wavelength in a ground state. If the reflectance varies from the maximum value by 10% or more within the range, the emission spectrum of the SLD can be effectively changed.

In Examples 1 to 3 described above, an SLD is formed on a GaAs substrate. The present invention, however, can also achieve effects in an SLD made of any other material formed on an InP substrate or a GaN substrate. Therefore, the present invention is not limited to an SLD formed on a GaAs substrate, and the emission wavelength band of an active layer is not limited to 1050 nm.

An active layer structure is not limited to a quantum well structure as in Examples 1 to 3 described above. The active layer structure may be a bulk structure or a confined structure other than a quantum well structure, such as a quantum wire structure or a quantum dot structure. In this case, the maximum value of a reflectance spectrum at a rear edge needs to fall within a wavelength range where a gain spectrum is positive at an active layer under an SLD drive condition.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-028730, filed Feb. 13, 2012, which is hereby incorporated by reference herein in its entirety.

What is claimed is:

1. A superluminescent diode which amplifies light through stimulated amplification and outputs emitted beams from one of edges at two ends, comprising:

a cladding layer of a first conductivity type formed on a semiconductor substrate;

an active layer formed on the cladding layer of the first conductivity type;

a cladding layer of a second conductivity type formed on the active layer; and a multilayer film formed at the other edge opposite to the one edge that emits the beams, reflectance of which has wavelength dependence, wherein the multilayer film is configured such that a spectral shape of the emitted beams output from the one edge is controllable thereby.

2. The superluminescent diode according to claim 1, wherein the multilayer film is further configured such that, a wavelength range of a high reflectance band of the multilayer film and a wavelength range of a spectrum of the emitted beams at least partially overlap each other, and the wavelength range of the high reflectance band of the multilayer film is narrower than the wavelength range of the spectrum of the emitted beams.

3. The superluminescent diode according to claim 2, wherein the active layer is configured such that a wavelength range between, a longest one of wavelengths in ground states of quantum wells constituting the active layer, and a shortest one of wavelengths in first states of the quantum wells constituting the active layer, is broader than the wavelength range of the high reflectance band of the multilayer film.

4. The superluminescent diode according to claim 2, wherein the high reflectance band covers a wavelength corresponding to a local minimum of a gain spectrum at the active layer under a device drive condition.

5. The superluminescent diode according to claim 2, wherein the active layer is configured such that a longest one of wavelengths in ground states of quantum wells constituting the active layer is longer than a wavelength within the wavelength range of the high reflectance band of the multilayer film, and a shortest one of wavelengths in first states of the quantum wells constituting the active layer is shorter than a wavelength within the wavelength range of the high reflectance band of the multilayer film.

6. The superluminescent diode according to claim 2, wherein the active layer includes a single quantum well or a plurality of quantum wells having the same structure, and at least a part of the high reflectance band is located between a wavelength corresponding to a ground state and a wavelength corresponding to a first state.

7. The superluminescent diode according to claim 2, wherein the active layer includes a plurality of quantum wells, a wavelength corresponding to one with a largest gain of ground states and first states of the quantum wells is present outside the high reflectance band, and a wavelength corresponding to at least one of the other states is present within the high reflectance band.

8. The superluminescent diode according to claim 1, wherein the multilayer film is further configured such that the wavelength dependence of the reflectance is a variability of 10% or more.

9. The superluminescent diode according to claim 2, wherein the active layer is configured such that height of the spectrum in the high reflectance band is made larger than in a case without the multilayer film by setting the high reflectance band in a wavelength region where a gain of the active layer is lower than a peak value.

10. The superluminescent diode according to claim 1, wherein the cladding layer of the first conductivity type is formed on a GaAs substrate.

11. An optical coherence tomography apparatus including a superluminescent diode according to claim 1.

12. A diode emitting light from one of edges at two ends, comprising:

a cladding layer of a first conductivity type formed on a semiconductor substrate;

an active layer formed on the cladding layer of the first conductivity type;

a cladding layer of a second conductivity type formed on the active layer; and a multilayer film formed at the other edge opposite to the one edge that emits light, reflectance of which has wavelength dependence, wherein an AR coating is applied to the one edge such that the AR coating allows the one edge to achieve a reflectance of not more than 0.05, and wherein the diode is a superluminescent diode which amplifies light through stimulated amplification and outputs emitted light.

13. The diode according to claim 12, wherein the diode emits from the one edge light having a unimodal spectral shape or a spectral shape analogical to the shape of a Gaussian function from the one edge.

14. The diode according to claim 12, wherein the cladding layer of a second conductivity type has a ridge shape.

15. The diode according to claim 12, wherein the multilayer film is a reflector designed such that the diode emits from the one edge light having a spectral shape which is made closer to a unimodal spectral shape or a spectral shape analogical to the shape of a Gaussian function.

16. The diode according to claim 12, wherein the active layer is configured such that a wavelength range between, a longest one of wavelengths in ground states of quantum wells constituting the active layer, and a shortest one of wavelengths in first states of the quantum wells constituting the active layer, is broader than the wavelength range of a high reflectance band of the multilayer film.

17. The diode according to claim 12, wherein the multilayer film is formed by stacking SiOxNy layers.

18. The diode according to claim 12, wherein the active layer forms an asymmetric multiple quantum well.

* * * * *